US006962686B2

(12) United States Patent  
Kayyem et al.

(10) Patent No.: US 6,962,686 B2  
(45) Date of Patent: Nov. 8, 2005

(54) CELL-SPECIFIC GENE DELIVERY VEHICLES

(75) Inventors: Jon F. Kayyem, Pasadena, CA (US); Thomas J. Meade, Altadena, CA (US); Scott E. Fraser, Newport Beach, CA (US)

(73) Assignee: California Institute of Technology, Pasadena, CA (US)

( * ) Notice: Subject to any disclaimer, the term of this patent is extended or adjusted under 35 U.S.C. 154(b) by 174 days.

(21) Appl. No.: 08/541,191

(22) Filed: Oct. 11, 1995

(65) Prior Publication Data

US 2005/0074403 A1 Apr. 7, 2005

Related U.S. Application Data

(63) Continuation-in-part of application No. 08/321,552, filed on Oct. 12, 1994, now Pat. No. 6,232,295.

(51) Int. Cl.[7] ..................... A61K 51/00; A61M 36/14
(52) U.S. Cl. .................. 424/1.69; 424/1.11; 424/1.65; 424/1.73
(58) Field of Search .............................. 424/1.11, 1.65, 424/1.73, 9.1, 9.3, 9.34, 9.5, 9.6; 530/300, 530/324–330; 534/10–16, 7; 536/22.1, 25.6, 536/26.1, 27.1, 23.1

(56) References Cited

U.S. PATENT DOCUMENTS

| | | | | |
|---|---|---|---|---|
| 4,104,466 | A | | 8/1978 | Tsuchida et al. ............ 542/433 |
| 4,284,537 | A | | 8/1981 | Beachey ........................ 260/6 |
| 4,701,521 | A | * | 10/1987 | Ryser et al. ................. 530/300 |
| 4,847,240 | A | * | 7/1989 | Ryser et al. ................. 530/300 |
| 5,059,415 | A | | 10/1991 | Neuwelt ......................... 424/9 |
| 5,155,215 | A | * | 10/1992 | Ranney ....................... 424/9.1 |
| 5,230,883 | A | * | 7/1993 | Kornguth et al. .............. 424/9 |
| 5,241,060 | A | * | 8/1993 | Engelhardt et al. ......... 536/27.1 |
| 5,274,119 | A | * | 12/1993 | Frazier et al. ............... 548/521 |
| 5,358,704 | A | * | 10/1994 | Desreux et al. .............. 424/9.1 |
| 5,373,093 | A | * | 12/1994 | Vallarino et al. ............. 534/10 |
| 5,521,291 | A | * | 5/1996 | Curiel et al. ............... 536/22.1 |

FOREIGN PATENT DOCUMENTS

| EP | 0253202 | 1/1988 |
|---|---|---|
| EP | 0388758 | 9/1990 |
| WO | 9301837 | 2/1993 |

OTHER PUBLICATIONS

Wagner et al (1990), Proc. Natl. Acad. Sci. USA, vol. 87, pp. 3410-3414, Transferrm-Polycation Conjugates as Carriers for DNA Uptake.*
Wogner et al(1991), Proc.Natl.Acad. Sci. USA, vol. 88,pp. 4255-4259, "Transferrin-Polycation-DNA Complexes: The Effect of Polycations on the Structure of the Complex and DNA Delivery to Cells."*
Panday et al (1986). Journal of Immunological Methods, vol. 94, pp. 237-246, "Photo-Chemical Linking of Primary Aromatic Amines to Carrier Proteins to Elicit Antibody Response Against the Amine Haptens."*
Hratowich et al (1983), Journal of Immunoogical Methods, vol. 65, pp. 147-157, "The Preparation of DTPA-Coupled Antibodies Radiolabeled With Metallic Radonuclides: an Improved Method".*
Cotton et al (Jun. 1990), Proc. Natl. Acad. Sci. USA, vol. 87, pp. 4033-4037, "Transferrin-Poly Cation-Mediated Introduction of DNA into Human Leukemic Cells: Stimulation by Agents That Affect the Survival of Transfected DNA or Modulate Transferrin Receptor Levels."*
Wu et al. J. Biol. Chem., 226(22):14338-14342, 1991.*
Diwu, Z. And J. W. Lown, "Phototherapeutic Potential of Alternative Photosensitizers to Porphyrins," *Pharmac. Ther.*, 63:1-35 (1994).
Goldenberg, D.M., et al., "Targeting Cancer wit Radiolabeled Antibodies," 5th Conference on Radioimmunodetection and Radioimmunotherapy of Cancer, Princeton, N.J., USA (Oct. 6-8, 1994).
Grossweiner, L.I., "Photodynamic Therapy with Porphyrin Derivatives," *Porphyric Pesticides*, Ch. 18 255-265 (1994).
Hung,M-C., et al., "HER-2/Neu-Targeting Gene Therapy—a Review," *Gene*, 159:65-71 (1995).
Kayyem, J.F., et al., "Receptor-Targeting Co-Transport of DNA and Magnetic Resonance Contrast Agents," *Chemistry & Biology*, 2:615-620 (1995).
Kemshead, J.T., and K. Hopkins, "Uses and Limitations of Monoclonal Antibodies (MoAbs) in the Treatment of Malignant Disease: A Review," *Journal of the Royal Society of Medicine*, 86:219-224 (1993).
King, D.J., et al., "Improved Tumor Targeting with Chemically Cross-Linked Recombinant Antibody Fragments," *Cancer Research*, 54:6176-6185 (1994).
Larson, S.W., "Radioimmunology," *Cancer*, 67:1253-1260 (1991).

(Continued)

Primary Examiner—Dameron L. Jones
(74) Attorney, Agent, or Firm—Dorsey & Whitney LLP; Richard F. Trecartin; Robin M. Silva

(57) ABSTRACT

A delivery vehicle is described that is capable of being specifically bound to and taken into targeted cells, delivering numerous physiological agents, particularly paramagnetic ions for magnetic resonance imaging (MRI) of the cells. The delivery vehicle comprises a polymeric molecule having a net positive charge complexed with another polymeric molecule having a net negative charge. Cell targeting moieties and physiological agents, including contrast agents and therapeutic agents, are attached to one or both of the polymeric molecules. In one embodiment, the polymeric molecule having a net negative charge is a nucleic acid. Thus, the delivery vehicles can be used in clinical protocols in which nucleic acids for gene therapy and agents for MRI contrast are co-transported to specific cells allowing medical imaging monitoring of nucleic acid delivery.

3 Claims, 4 Drawing Sheets

OTHER PUBLICATIONS

Ludlow, J.W. and G.R. Skuse, "Viral Oncoprotein binding to pRB, p107, p130, and p300," *Virus Research*, 35:113-121 (1995).

Schott, M.E., et al., "Biodistribution and Preclinical Radioimmunotherapy Studies Using Radiolanthanide-Labeled Immunoconjugates," *Cancer*, 73(3):993-998 (1994).

Jurcic, J.G. and Scheinberg, D.A., "Recent Developments in the Radioimmunotherapy of Cancer," *Current Opinion in Immunology*, 6:715-721 (1994).

Thomas, H., and Sikora, K., "New Therapeutic Modalities for Cancer," *Reviews in Oncology*, 4(1):107-120 (1991).

Uckun, F.M., et al., "Biotherapy of B-Cell Precursor Leukemia by Targeting Genistein to CD19-Associated Tyrosine Kinases," *Science*, 267:886-891 (1995).

Uckun, F.M., "Immunotoxins for the Treatment of Leukaemia," *British Journal of Haematology*, 85:435-438 (1993).

Urban, J.L., "Tumor Antigens," *Annu. Rev. Immunol.*, 10:617-644 (1991).

Wilbur, D.S., et al., "Monoclonal Antibody Fab' Fragment Cross-Linking Using Equilibrium Transfer Alkylation Reagents. A Strategy for Site-Specific Conjugation of Diagnostic and Therapeutic Agents with $F(ab')_2$ Fragments," *Bioconjugate Chem.*, 5:220-235 (1994).

Wagner, E., et al., "Influenza Virus Hemagglutinin HA-2 N-Terminal Fusogenic Peptides Augment Gene Transfer by Transferrin-Polylysine-DNA Complexes: Toward a Synthetic Virus-Like Gene-Transfer Vehicle," *Proc. Natl. Acad. Sci. USA*, 89:7934-7938 (1992).

Wu, C., et al., "Metal-Chelate-Dendrimer-Antibody Constructs for Use in Radioimmunotherapy and Imaging," *Bioorganic and Medicinal Chemistry Letters*, 4(3):449-454 (1994).

Wu, G.W., et al., "Receptor-Mediated Gene Delivery in Vivo," *J. Biol. Chem.*, 266(22):14338-14342 (1991).

Kumar, K., et al., "Ligand Basicity and Rigidity Control Formation of Macrocyclic Polyamino Carboxylate Complexes of Gadolinium (III)", *Inorg. Chem.*, 32:4193-4199 (1993).

Lex, L., "Development of Contrast Enhancing Agents in Magnetic Resonance Imaging," *Acta Biochim. Biophys. Hun.*, 24/3:265-281 (1989).

Grossweiner, L.I., "Photodynamic Therapy with Porphyrin Derivatives," *American Porphyric Pesticides*, Ch. 18:225-265 (1994).

Paajanen, H., et al., "Proton Relaxation Enhancement of Albumin, Immunoglobulin G, and Fibrinogen Labeled with Gd-DTPA," *Magnetic Resonance in Medicine*, 13:38-43 (1990).

Behr, Jean-Paul, "Gene Transfer with Synthetic Cationic Amphiphiles: Prospects for Gene Therapy," *Bioconjugate Chem.*, 5:382-389 (1994).

Schwendener, R.A., "Liposomes and Immunoliposomes as Carriers for Cytostatic Drugs, Magnetic Resonance Contrast Agents, and Fluorescent Chelates," *Chimia*, 46:69-77 (1992).

Zatloukal, K., et al., "Somatic Gene Therapy for Cancer: The Utility of Transferrinfection in Generating 'Tumor Vaccines'," *Gene*, 135:199-207 (1993).

DeMagalhaes-Silverman, M., et al., "Bone Marrow Transplantation a Review," *Cell Transplantation*, 2:75-98 (1993).

Gutierrez, A.A., et al., "Gene Therapy for Cancer," *The Lancet*, 339:715-721 (1992).

Renn, O., et al., "Large-Scale Synthesis of the Bifunctional Chelating Agent 2-(p-Nitrobenzyl)-1,4,7,10-tetraazacyclododecane-N,N',N'',N'''-tetraacetic Acid, and the Determination of Its Enantiomeric Purity by Chiral Chromatography," *Bioconjugate Chem.*, 3:563-569 (1992).

McMurray, T.J., et al., "Convenient Synthesis of Bifunctional Tetraaza Macrocycles," *Bioconjugate Chem.*, 3:108-117 (1992).

Moi, M.K., et al., "The Peptide Way to Macrocyclic Bifunctional Chelating Agents: Synthesis of 2-(p-Nitrobenzyl)-1,4,7,10-tetraazacyclododecane-N,N',N'',N''',-tetraacetic Acid and Study of Its Yttrium (III) Complex," *J. Am. Chem. Soc.*, 110:6266-6267 (1988).

Tweedle, M.F., et al., "Considerations Involving Paramagnetic Coordination Compounds as Useful NMR Contrast Agents," *Nucl. Med. Biol.*, 15(1):31-36 (1988).

Cotten, M., et al., "High-Efficiency Receptor-Mediated Delivery of Small and Large (48 Kilobase Gene Constructs Using the Endosome-Disruption Activity of Defective or Chemically Inactivated Adenovirus Particles," *Proc. Natl. Acad Sci, USA.*, 89:6094-6098 (1992).

Wagner, E., et al., "Coupling of Adenovirus to Transferrin-Polylysine/DNA Complexes Greatly Enhances Receptor-Mediated Gene Delivery and Expression of Transfected Genes," *Proc. Natl. Acad. Sci., USA*, 89:6099-6103 (1992).

Wagner, E., et al., "DNA-Binding Transferrin Conjugates as Functional Gene-Delivery Agents: Synthesis by Linkage of Polylysine or Ethidium Homodimer to the Transferrin Carbohydrate Moiety," *Bioconjugate Chem.*, 2:226-231 (1991).

Weissleder, R., et al., "Drug Targeting in Magnetic Resonance Imaging," *Magnetic Resonance Quarterly*, 8(1):55-63 (1992).

Zenke, M., et al., "Receptor-Mediated Endocytosis of Transferrin-Polycation Conjugates: An Efficient Way to Introduce DNA into Hematopoietic Cells," *Proc. Natl. Acad. Sci. USA*, 87:3655-3659 (1990).

Wagner, E., et al., "Transferrin-polycation-DNA Complexes: The Effect of Polycations on the Structure of the Complex and DNA Delivery to Cells," *Proc. Natl. Acad. Sci. USA*, 88:4255-4259 (1991).

Oser, A., et al., "Sensitive Non-Radioactive Dot-Blot Hybridization Using DNA Probes Labelled with Chelate Group Substituted Psoralen and Quantitative Detection by Europium Ion Fluorescence," *Nucleic Acids Research*, 16(3):1181-1196 (1988).

Nabel, E.G., "Gene Therapy for Cardiovascular Disease," *Circulation*, 9(2):541-548 (1995).

Curiel, D.T., et al., "Gene Transfer to Respiratory Epithelial Cells via the Receptor-Mediated Endocytosis Pathway," *American Journal of Respiratory Cell and Molecular Biology*, 6:247-252 (1992).

Curiel, D.T., et al., "Adenovirus Enhancement of Transferrin-Polylysine-Mediated Gene Delivery," *Proc. Natl. Acad. Sci. USA*, 88:8850-8854 (1991).

Cotten, M., et al., "Receptor-Mediated Transport of DNA into Eurkaryotic Cells," *Methods in Enzymology*, 217:618-645 (1993).

Hnatowich, D.J., et al., "The Preparation of DTPA-Coupled Antibodies Radiolabeled with Metallic Radionuclides: and Improved Method," *Journal of Immunological Methods*, 65:147-157 (1983).

Kabanov, A.V., et al., "DNA Interpolyelectrolyte Complexes as a Tool for Efficient Cell Transformation," *Biopolymers*, 31:1437-1443 (1991).

Kahn, M.L., et al., "Optimization of Retroviral Vector-Mediated Gene Transfer into Endothelial Cells in Vitro," *Circulation Research*, 71:(6):1508-1517 (1992).

Shen, T., et al., "Monocrystalline Iron Oxide Nanocompounds (MION): Physicochemical Properties," *MRM*, 29:599-604 (1993).

Slinkin, M.A., et al., "Terminal-Modified Polylysine-Based Chelating Polymers: Highly Efficient Coupling to Antibody with Minimal Loss in Immunoreactivity," *Bioconjugate Chem.*, 2:342-348 (1991).

Torchilin, V.P., et al., "The Antibody-Linked Chelating Polymers for Nuclear Therapy and Diagnostics," *Critical Reviews in Therapeutic Drug Carrier System*, 7(4):275-308 (1991).

Torchilin, V.P., et al., "Monoclonal Antibody Modification with Chelate-Linked High-Molecular-Weight Polymers: Major Increases in Polyvalent Cation Binding without Loss of Antigen Binding," *Hybridoma*, 6(3):229-240 (1987).

Trubetskoy, V.S., et al., "Catonic Liposomes Enhance Targeted Delivery and Expression of Exogenous DNA Mediated by N-Terminal Modified Poly(L-lysine)-Antibody Conjugate in Mouse Lung Endothelial Cells," *Biochimica et Biophysica Acta.*, 1131:311-313 (1992).

Trubetskoy, V.S., et al., "Use of N-Terminal Modified Poly (L-lysine)-Antibody Conjugate as a Carrier for Targeted Gene Delivery in Mouse Lung Endothelial Cells," *Bioconjugate Chem.*, 3:323-327 (1992).

Unger, E.C., et al., "Magnetic Resonance Imaging Using Gadolinium Labeled Monoclonal Antibody," *Investigative Radiology*, 693-700 (1985).

Wagner, E., et al., "Transferrin-Polycation Conjugates as Carriers for DNA Uptake into Cells," *PNAS, USA*, 87:3410-3414 (1990).

Heindel, N.D., et al., "Macromolecular Attachment as a Metabolic Stabilizer for a Labile Radiosensitizer," *J. Pharm. Sci.*, 76(5):384-386 (1987).

Hamblin, M.R., et al., "Photosensitizer Targeting in Photodynamic Therapy: I. Conjugates of Haematoporphyrin with Albumin and Transferrin," *Journal of Photochemistry and Photobiology*, 26:45-56 (1994).

Flynn, G., et al., "Magnetically Responsive Photosensitizing Reagents for Possible Use in Photoradiation Therapy," *Cancer Letters*, 78:109-114 (1994).

Hamblin, M.R., et al., "In Preparation of Site-Specific Monoclonal Antibody Hematoporphyrin Conjugates via Poly-Lysine Linkers," *Journal of Photochemistry and Photobiology*, 61(5)(Supp.):95S, Abstract No.: WPM-D6 (1995).

* cited by examiner

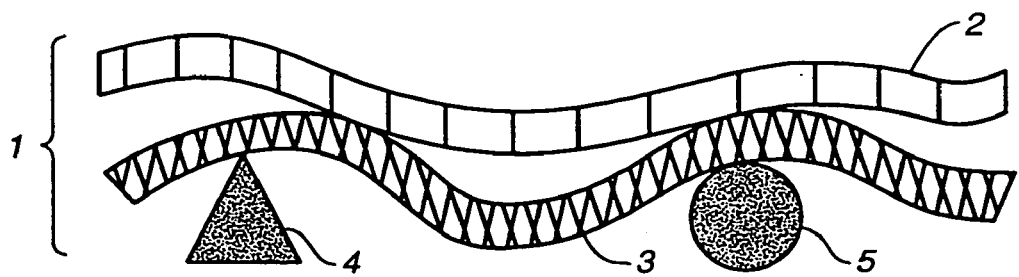
FIG._1A
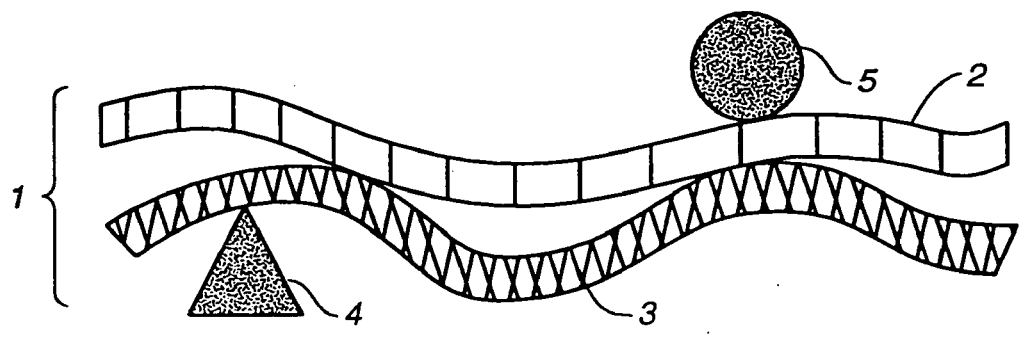
FIG._1B
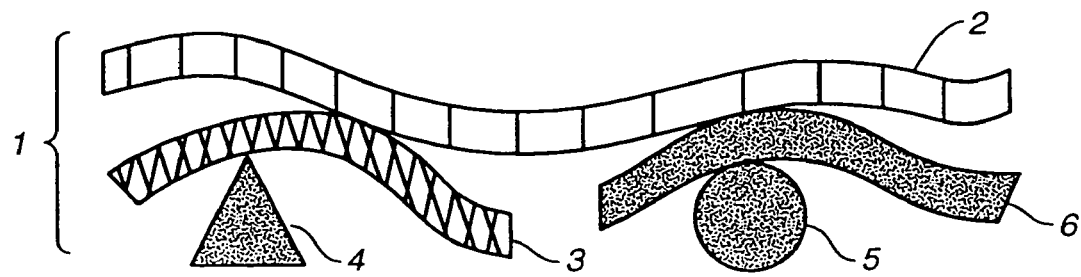
FIG._1C

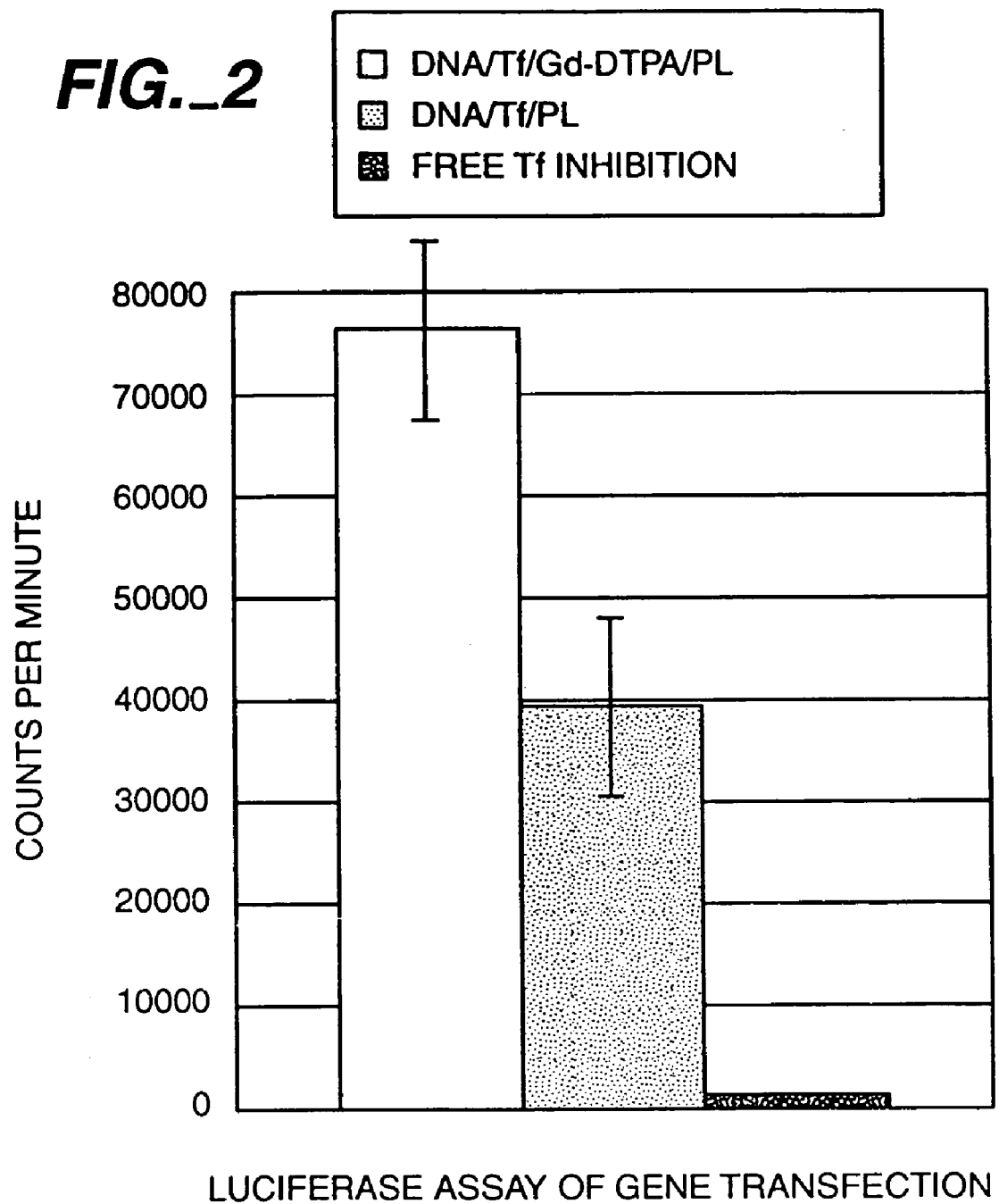

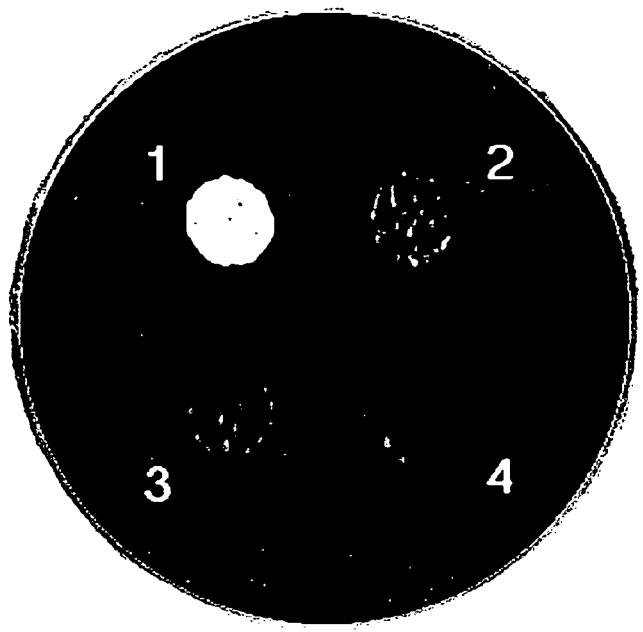
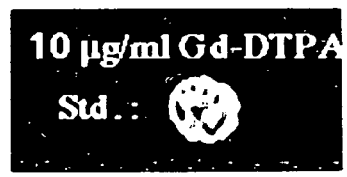
1: Gd-DTPA-PLL/
 Tf-PLL/DNA
2: Gd-DTPA-PLL/
 Tf-PLL/DNA
 + free Tf
3: PLL/Tf-PLL/DNA
4: PLL/Tf-PLL/DNA
 + free Tf
FIG._3

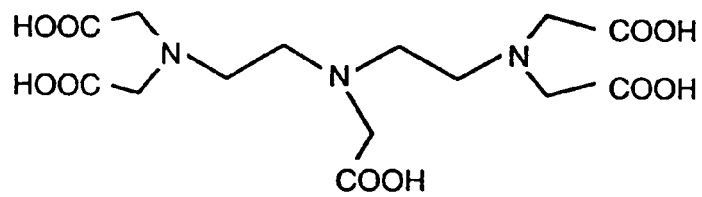
DTPA
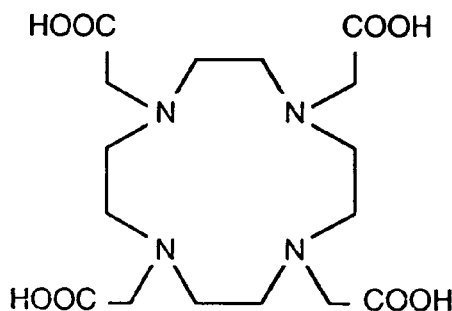
DOTA
FIG._4
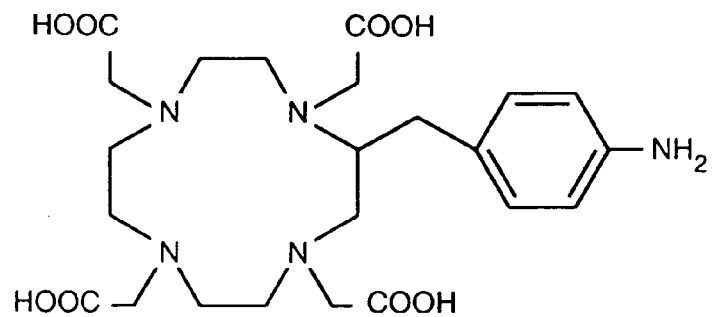
p-aminobenzyl-DOTA

CELL-SPECIFIC GENE DELIVERY VEHICLES

This application is a continuation-in-part application of U.S. Ser. No. 08/321,552, filed Oct. 12, 1994 now U.S. Pat. No. 6,232,295.

BACKGROUND OF THE INVENTION

In recent years, magnetic resonance imaging (MRI) has emerged as a powerful tool in clinical settings because it is noninvasive and yields an accurate volume rendering of the subject. The image is created by imposing one or more orthogonal magnetic field gradients upon the specimen while exciting nuclear spins with radio frequency pulses as in a typical nuclear magnetic resonance (NMR) experiment. After collection of data with a variety of gradient fields, deconvolution yields a one, two, or three dimensional image of the specimen. Typically, the image is based upon the NMR signal from the protons of water where the signal intensity in a given volume element is a function of the water concentration and relaxation times ($T_1$ and $T_2$). Local variations in these three parameters provide the vivid contrast observed in MR images. For example, the low water content of bone makes it distinctively dark, while the short $T_2$ of clotted blood affords it a higher signal intensity than that from non-clotted blood.

The same advantages that have made MRI the technique of choice in medical imaging make it an ideal imaging tool for use in biological experiments. Unlike light-microscope imaging techniques based upon the use of dyes or fluorochromes, MRI does not produce toxic photobleaching byproducts. Furthermore, unlike light-microscopy, MRI is not limited by light scattering or other optical aberrations to cells within approximately only one hundred microns of the surface.

MRI was originally considered a purely noninvasive approach but more recently it has been found that contrast agents can significantly improve the diagnostic utility of the technique. MRI contrast agents dramatically reduce the relaxation times of protons in the surrounding water. The ion $Gd^{3+}$, in its non-toxic chelated forms, is the most commonly used paramagnetic ion because of its large magnetic dipole and large effect on relaxation times. For example, $Gd^{3+}$ chelated with diethylenetriaminepentaacetic acid (DTPA) is a vascular contrast agent now widely used in diagnostic radiology. The chemical structure of DTPA is depicted in FIG. 4.

Traditional MRI offers high spatial resolution and multiple plane imaging in a fast noninvasive procedure. When MRI contrast agents are used diagnostically, they are vascularly perfused, enhancing the contrast of blood vessels and reporting on organ lesions and infiltration. However, the labeling of specific tissues for diagnostic radiology remains a difficult challenge for MRI. Efforts to develop cell and tissue-specific MRI contrast agents by modifying existing immunological techniques has been the focus of much research in diagnostic radiology. For example, antibodies labeled with paramagnetic ions, generally the gadolinium chelate Gd-DTPA, have been generated and tested for their effects on MRI contrast of tumors and other tissues [Lex, Acta Biochim. Biophys. Hung. 24:265–281 (1989); U.S. Pat. No. 5,059,415]. It was anticipated that due to reductions in the rate of molecular tumbling, Gd-DTPA when bound to antibodies would show significantly higher relaxivity, a measure of MRI contrast enhancement, than that of unbound Gd-DTPA. This increase in relaxivity per Gd ion, it was hoped, would generate sufficient signal for tissue contrast to be observed using antibodies labeled with 10–50 Gd ions per protein molecule.

Unfortunately, the relaxivity of Gd bound to antibodies has been found to be only slightly better than that of unbound Gd-DTPA [Paajanen et al., Magn. Reson. Med 13:38–43 (1990)]. Therefore, to generate detectable contrast enhancement in an antibody-labeled tissue, the immunological reagent must be conjugated with hundreds if not thousands of Gd ions per antibody. Currently this is unattainable using standard techniques.

Several researchers have examined the possibility that the number of Gd ions per antibody could be increased by conjugating polylysine to the antibody, then labeling the polylysine extensively with Gd-DTPA [WO93/01837]. So far, these attempts have shown only limited success in part due to the unfavorable ionic and steric effects of conjugating antibodies to large polymers.

Research in the field of targeted MRI contrast agents has thus turned to the use of iron oxide particles as high signal strength $T_2$ contrast agents [Shen et al., Magnet. Res. Med. 29:599–604 (1993); Weissleder et al., Magnetic Resonance Quarterly, 8:55–63 (1992)]. However, no iron oxide particles have yet been approved for use in humans.

Liposomes as carriers of contrast media show promise as tissue-specific MRI agents as well [Schwendener, R. A., Chimia 46:69–77 (1992)]. Two classes of such contrast agents have been developed: (i) water soluble contrast agents entrapped between phospholipid bilayers, and (ii) liposomes directly incorporating amphipatic molecules covalently attached to MRI contrast agents such as Gd-DTPA. The former class of liposomal contrast agents suffers from leakiness of the water soluble agent in vivo, and the later from long-term retention of the agent in the liver and spleen. Nevertheless, liposomes show promise as liver, spleen and lung contrast agents.

In addition, a number of researchers have explored the delivery of nucleic acids using polylysine. For example, polylysine coupled to ligands for cell-surface receptors such as transferrin [Wagner et al., Proc. Natl. Acad. Sci. USA 87:3410–3414 (1991)] and asialoglycoprotein [Wu et al., J. Biol. Chem. 266:14338–14342 (1991)] facilitate the receptor mediated uptake of DNA. The —$NH^{3+}$ groups of the lysine side chains at neutral pH are used to complex with the negatively charged phosphate backbone of the DNA. Electrically neutral complexes of the polyanionic DNA and the polycationic polylysine-protein conjugates form what is thought to be toroidal particles capable of delivering DNA into specific cells at relatively high efficiency [Wagner et al., Proc. Natl. Acad. Sci. USA 88:4255–4259 (1991)]. Improvements to this technique include complex formation with hydrophobic polycations to increase transfection efficiency and cotransfection with adenovirus particles [Wagner et al., Proc. Natl. Acad. Sci. USA 89:6099–6103 (1992)] or conjugation of fusogenic peptides to the polylysine [Wagner et al., Proc. Natl. Acad. Sci. USA 89:7934–7938 (1992)] or transfection in the presence of chloroquine [Wagner et al., Proc. Natl. Acad. Sci. USA 87:3410–3414 (1991)], all to reduce endosomal degradation of the DNA. It has been noticed that modifications to these particles which promote escape from lysosomal degradation pathways can increase gene expression (Wagner et al. PNAS 89:7934–7938 (1992)].

SUMMARY OF THE INVENTION

Based on the foregoing it is apparent that there exists a need for improved cell- and tissue-specific delivery of physiological agents. Accordingly, it is an object of the invention to provide tissue-specific delivery vehicles that are capable of binding multiple physiological agents without losing tissue-specificity.

It is a further object of the invention to provide novel delivery vehicles comprising tissue-specific cell targeting moieties and contrast agents attached to nucleic acids to provide delivery vehicles useful in gene delivery and therapy. Such gene delivery can be monitored by way of the presence or absence of the contrast agent.

It is an additional object to provide novel delivery vehicles comprising tissue-specific cell targeting moieties and therapeutic agents to provide delivery vehicles useful in the treatment of cancer.

These and other objects and features of the invention will become apparent to those skilled in the art from the following detailed description and appended claims.

The objects are achieved by cell-specific delivery vehicles and methods wherein such delivery vehicles are capable of delivering at least an imaging contrast agent to the targeted cell or tissue. In some embodiments the delivery vehicle is constructed to deliver additional specific molecules (e.g. nucleic acids).

In one embodiment of the invention, a delivery vehicle is provided comprising a) a first polymeric molecule having a net positive or negative charge, b) at least one second polymeric molecule having a net charge opposite that of the first polymeric molecule and complexed with the first polymeric molecule, the second polymeric molecule having attached thereto at least one cell targeting moiety, and c) at least one physiological agent attached to the first or second polymeric molecule (see FIGS. 1A and 1B) or to a third polymeric molecule (see FIG. 1C), wherein the third polymeric molecule, if present, has a net charge opposite that of the first polymeric molecule and is complexed with the first polymeric molecule.

In another embodiment, one of the polymeric molecules comprises a nucleic acid which is complexed with one or more polymeric molecules comprising a polyamine, so that the resulting contrast agent delivery vehicle is capable of delivering genetic material as well as a physiological agent in a cell or tissue-specific manner.

In a further embodiment, the invention provides methods of delivering physiological agents to a cell. The method comprises contacting the cell with a delivery vehicle of the invention, and detecting the presence of the physiological agent.

BRIEF DESCRIPTION OF THE DRAWINGS

FIG. 1A depicts a delivery vehicle (1) wherein a first polymeric molecule (2) having a net positive or a net negative charge is complexed with a second polymeric molecule (3) having a net charge opposite that of the first polymeric molecule. At least one cell targeting moiety (4) and at least one contrast agent (5) are attached to the second polymeric molecule.

FIG. 1B depicts a delivery vehicle (1) wherein a first polymeric molecule (2) having a net positive or a net negative charge is complexed with a second polymeric molecule (2) having a net charge opposite that of the first polymeric molecule. At least one cell targeting moiety (3) is attached to the second polymeric molecule and at least one contrast agent (4) are attached to the first polymeric molecule.

FIG. 1C depicts a delivery vehicle (1) wherein a first polymeric molecule (2) having a net positive or a net negative charge is complexed with a second polymeric molecule (3) having a net charge opposite that of the first polymeric molecule. A third polymeric molecule (6) having a charge opposite that of the first polymeric molecule is complexed with the first polymeric molecule. At least one cell targeting moiety (4) is attached to the first polymeric molecule and at least one MRI contrast agent (5) is attached to the third polymeric molecule.

FIG. 2 compares the level of gene expression of cells transfected with DNA complexed with Gd-DTPA-poly-D-lysine (column 1) to cells transfected with particles which lack the Gd-DTPA-poly-D-Lysine component (column 2). In column 3, free transferrin was added to the solution to competitively inhibit uptake of the gene delivery vehicles (both with and without Gd-DTPA-poly-D-lysine). In all cases 6 $\mu$g of DNA was complexed with 3 $\mu$g transferrin polylysine (Tf) and 4 $\mu$g Gd-DTPA modified poly-D-lysine or unmodified poly-L-lysine (PLL). Error bars represent 1 standard deviation (n-5).

FIG. 3 compares the MRI image obtained from cells transfected with gene delivery-vehicles containing Gd-DTPA-poly-D-lysine (1 and 2) to those lacking the GD-DTPA-poly-D-lysine (3 and 4). Note the intense signal indicative of Gd contrast enhancement in 1. In 2 and 4, free transferrin was added to competitively inhibit uptake of the particle. In all cases 12 $\mu$g of DNA was complexed with 6 $\mu$g transferrin polylysine and 14 $\mu$g Gd-DTPA modified poly-D-lysine or unmodified poly-L-lysine.

FIG. 4 depicts the Gd chelating agents, diethylenetriaminepentaacetic acid (DTPA) and 1,4,7,10-tetraazacyclododecane —N,N',N'',N'''-tetracetic acid (DOTA), and p-aminobenzyl-DOTA.

DETAILED DESCRIPTION OF THE INVENTION

Prior to the invention, there were no safe and effective means for targeted delivery of physiological agents to specific cells or tissue using cell-surface receptors. The present invention provides delivery vehicles and methods for the delivery of physiological agents, including contrast agents and therapeutic agents, to a cell. The delivery vehicles comprise two or more polymeric molecules, a cell targeting moiety, and a physiological agent. Accordingly, the delivery vehicles are targeted to a certain cell type, depending on the targeting moiety used, and then generally are taken up by the target cells. The physiological agent is thus targeted to a specific cell type.

The delivery vehicles of the present invention comprise a first polymeric molecule and a second polymeric molecule. As indicated in FIG. 1A, the delivery vehicle (1) comprises a first polymeric molecule (2) having an overall net positive or negative charge which is employed as a scaffold to which an oppositely charged second polymeric molecule (3) is complexed. As shown in FIG. 1B, some delivery vehicles include a third polymeric molecule (6) having a net charge opposite that of the first polymeric molecule and complexed with the first polymeric molecule. Preferably the first and second polymeric molecules are held together by electrostatic interactions and thus do not need to be covalently linked to each other. In certain embodiments, both the first and second polymeric molecules contain a mixture of charged groups and thus are zwitterionic. The depiction of linear polymeric molecules in FIG. 1 is for illustrative purposes and is not necessarily preferred, as circular polymers such as plasmids may also be used. The delivery vehicle will be in any configuration that is suitable for cellular uptake.

In a preferred embodiment, the first polymeric molecule is polyanionic (i.e. a polymer having a net negative charge). In this embodiment, the polyanion comprises a molecule based on heparin, polygalacturonic acid, mucin, nucleic acids and their analogs including those with modified ribose-phosphate backbones, the polypeptides polyglutamate and polyaspartate, as well as carboxylic acid, phosphoric acid, and sulfonic acid derivatives of synthetic polymers. Preferred polyanions are nucleic acids. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Specifically included within the definition of nucleic acids are anti-sense nucleic acids. An anti-sense nucleic acid will hybridize to the non-coding strand of a nucleic acid, but may contain ribonucleotides as well as deoxyribonucleotides. Generally, antisense nucleic acids function to prevent gene expression or translation of mRNA. The nucleic acid may be double stranded, single stranded, or contain portions of both double stranded or single stranded sequence. In a preferred embodiment, the nucleic acid is double stranded, most preferably a double stranded plasmid.

When RNA or DNA is used as the first polymeric molecule, the nucleic acid can serve additional functions. In one embodiment, the nucleic acid encodes a reporter gene, such that the uptake of the delivery vehicle can be additionally monitored by the presence or absence of the reporter gene and/or the protein encoded by the gene. For example, as depicted in the Examples, the reporter gene encoding luciferase may be used. In addition, DNA or RNA sequences encoding selectable markers can be delivered as well, providing a means to select transfected cells in vitro prior to tissue or cell transplantation. [Demagalhaessilverman et al. "Bone-Marrow Transplantation—A Review" *Cell Transplantation* 2:75–98 (1993)].

In a preferred embodiment, the delivery vehicles of the invention can perform the additional function of delivering genetic material to a cell. Hence, this embodiment encourages a novel clinical protocol in which nucleic acids for gene therapy and agents for MRI contrast are co-transported to specific cells (e.g., cells of a neoplastic tumor) allowing medical imaging monitoring of nucleic acid delivery and therapy in real time.

In a preferred embodiment, the nucleic acid is used as a therapeutic agent of sorts. For example, clinical uses of the invention may involve nucleic acids for gene therapy such as genes for lymphokines, growth hormones, exogenous antigens, viral enzymes (susceptibility genes), and genetic regulators, etc. Numerous reference are available that disclose the clinical potentials of gene therapy [e.g. Gutierrez et al. "Gene-Therapy for Cancer" *Lancet* 339:715–721 (1992); Zatloukal et al. "Somatic Gene-Therapy for Cancer—The Utility of Transferrinfection in Generating Tumor Vaccines: *Gene* 135:199–207 (1993)]. In particular, the nucleic acids comprise wild-type genes for genetic disorders caused by mutations such as cystic fibrosis and sickle cell anemia, among others.

In a preferred embodiment, the nucleic acid contains a gene encoding a product that can kill a cell containing the gene under the appropriate conditions. In a preferred embodiment, the nucleic acid of the delivery vehicle encodes the herpes virus thymidine kinase (TK) gene. Cells which contain this gene are sensitive to gancyclovir; that is, cells expressing TK are killed in the presence of gancyclovir. Thus, in a preferred embodiment, delivery vehicles containing contrast agents are targeted, as outlined herein, to tumor cells. When the contrast signal levels in the tumor are sufficiently high, gancyclovir is administered to kill the tumor cells. Similarly, the Gpt gene renders cells sensitive to 6-thioxanthine. A further advantage of this approach is that the uptake of the drug and the demise of the tumor can be monitored in real time using the contrast agent.

In an alternate embodiment, therapeutic uses of the nucleic acid involves the use of antisense nucleic acids. As is known in the art, antisense nucleic acids are used to decrease or eliminate the expression of genes encoding specific proteins.

In some situations, it may be desirable to deliver RNA or single stranded DNA because of its short half-life. For example, one could transfect cells with the delivery vehicle and select for transfected cells or show that they were transfected by assaying, for example, for the presence of a reporter gene in the single stranded nucleic acid. In such situations, the transfected cells would not stably integrate the reporter gene. This would be advantageous in situations where wild type cells are desired, such as in tissue grafting and stem cell therapy. In these cases, a utility of the delivery vehicle lies in the ability to readily label the cells with contrast agents, ultimately allowing non-invasive imaging of the grafted cells. Where no DNA integration is desired, other polyanions can be used such as polyaspartate, polyglutamate, heparin and long chain carbohydrates.

The polyanion acts as a negatively charged molecular scaffold to which a positively charged polymer (polycation) is complexed. Thus the polyanion and the polycation will have sufficient charge so that when combined, the two polymeric molecules form a polycomplex under physiological conditions. Generally, after complex formation, the polycomplexes are approximately electrically neutral, since electroneutrality is generally necessary to achieve high transfection efficiency (see Wagner et al., (1991), supra). As discussed below, the length and extent of derivatization of the polymers with cell targeting moieties and physiological agents may be varied to achieve electroneutrality.

Preferred polycations include synthetic polycations based on acrylamide and 2-acrylamido-2-methylpropanetrimethylamine, poly(N-ethyl-4-vinylpyridine) or similar quarternized polypyridine, diethylaminoethyl polymers and dextran conjugates, polymyxin B sulfate, lipopolyamines, poly (allylamines) such as the strong polycation poly (dimethyldiallylammonium chloride), polyethyleneimine, polybrene, spermine, spermidine and polypeptides such as protamine, the histone polypeptides, polylysine, polyarginine and polyornithine. Particularly preferred polycations are polylysine and spermidine, with the former being especially preferred. Both optical isomers of polylysine can be used. The D isomer has the advantage of having long-term resistance to cellular proteases. The L isomer has the advantage of being more rapidly cleared from the subject.

When polylysine is used as the second polymeric molecule, the —$NH_2$ groups of the lysine side chains at high pH serve as strong nucleophiles for multiple attachment of activated chelating agents. The invention takes advantage of both the polycationic and polynucleophilic nature of polyamines such as polylysine. At high pH the lysine monomers are coupled to the physiological agents under conditions that yield on average 5–20% monomer substitution. At physiologic pH to low pH, the remaining unlabeled positively charged lysines facilitate nucleic acid binding.

The size of the polyanion and polycation may vary substantially. For example, it is known that some nucleic acid vectors can deliver genes up to 100 kilobases in length, and artificial chromosomes (megabases) have been delivered to yeast. Therefore, there is no general size limit to the polyanion. However, for efficient receptor-mediated uptake, it is preferred that the nucleic acid be less than 100 kilobases, with from about 1 to about 50 kilobases being the most preferred size, and from about 5 to about 10 kilobases being particularly preferred. When polyanions other than nucleic acids are used, a preferred size for the polymer is from about 500 to about 50,000 monomer units, with from about 5,000 to about 20,000 being particularly preferred.

Generally the size of the polycation for nucleic acid complex formation will be less than about 500 monomer residues. When poly amino acids such as polylysine and polyarginine are used, preferred sizes are from about 10 to about 200 residues.

In a preferred embodiment, the delivery vehicles comprise a first polyanion molecule complexed to a second polycation molecule. The cell targeting moieties and physiological agents described below are attached to either polymeric molecule, although in a preferred embodiment they are both attached to the polycation. In alternative embodiments, they are both attached to the polyanion, or alternatively the cell targeting moiety is attached to one polymer and the physiological agent is attached to the other, as is depicted in FIG. 1.

In an alternate embodiment, the delivery vehicles comprise a first polymeric molecule and two or more second polymeric molecules with a net charge opposite to the charge of the first polymer. That is, as depicted in FIG. 1, it is possible to have multiple second polymeric molecules associated with the first polymeric molecule. In a preferred embodiment, the first polymeric molecule is polyanionic, and the second polymeric molecules are polycationic. In a preferred embodiment, the cell targeting moieties are added to one of the second polymeric molecules, and the physiological agents are added to another second polymeric molecule, although it is possible that each second polymeric molecule contains both.

As described above, in addition to the polymeric components, the delivery vehicles of the present invention physiological agents attached to one of the polymeric molecules. By the term "physiological agent" herein is meant compounds which are desirable to deliver in a cell-specific manner. Included in this definition of physiological agents are both contrast agents and therapeutic agents.

As used herein, the term "contrast agent" includes the various contrast agents that are known for medical imaging. For MRI, the contrast agent can comprise paramagnetic or superparamagnetic metals. By "paramagnetic metal ion", "paramagnetic ion" or "metal ion" herein is meant a metal ion which is magnetized parallel or antiparallel to a magnetic field to an extent proportional to the field. Generally, these are metal ions which have unpaired electrons; this is a term understood in the art. Examples of suitable paramagnetic metal ions, include, but are not limited to, gadolinium III (Gd+3 or Gd(III)), iron III (Fe+3 or Fe(III)), manganese II (Mn+2 or Mn(II)), yttrium III (Yt+3 or Yt(III)), dysprosium (Dy+3 or Dy(III)), chromium (Cr(III) or Cr+3). In a preferred embodiment the paramagnetic ion is the lanthanide atom Gd(III), due to its high magnetic moment ($u^2=63BM^2$), a symmetric electronic ground state ($S^8$), and its current approval for diagnostic use in humans.

Gd(III) ions are extremely toxic to cells and therefore must be bound to a chelating agent which is then conjugated to the polymeric molecule. There are a large number of known macrocyclic chelators or ligands which are used to chelate lanthanide and paramagnetic ions. See for example, Alexander, Chem. Rev. 95:273–342 (1995) and Jackels, Pharm. Med. Imag, Section III, Chap. 20, p645 (1990), expressly incorporated herein by reference, which describes a large number of macrocyclic chelators and their synthesis. Similarly, there are a number of patents which describe suitable chelators for use in the invention, including U.S. Pat. Nos. 5,155,215, 5,087,440, 5,219,553, 5,188,816, 4,885,363, 5,358,704, 5,262,532, and Meyer et al., Invest. Radiol. 25: S53 (1990), all of which are also expressly incorporated by reference. Thus, as will be understood by those in the art, any of the known paramagnetic metal ion chelators or lanthanide chelators can be used in the present invention. When the metal ion is Gd(III), a preferred chelator is 1,4,7,10-tetraazacyclododecane-N,N',N", N'''-tetracetic acid (DOTA) shown in FIG. 4. In an alternative embodiment, when the metal ion is Gd(III), preferred chelators include diethylenetriaminepentaacetic acid (DTPA) and 1,4, 7,10-tetraazacyclododecane-N,N',N",N'''-tetraethylphosphorus (DOTEP). The stability constant (K) for Gd(DTPA)$^{2-}$ is very high (logK=22.4) and is more commonly known as the formation constant. DOTA, DTPA and DOTEP may be substituted, as is known in the art; see for example, U.S. Pat. Nos. 5,262,532, 4,885,363, and 5,358,704.

Chelators for other paramagnetic ions are also known; see for example Lauffer et al., J. Am. Chem. Soc. 109:1622 (1987); Lauffer, Chem. Rev. 87:901–927 (1987); and U.S. Pat. Nos. 4,885,363, 5,358,704, and 5,262,532, all which describe chelators suitable for Fe(III) and Mn(II). Suitable chelators for Yt(III) ions include, but are not limited to, DOTA and DPTA and derivatives thereof (see Moi et al., J. Am. Chem. Soc. 110:6266–6267 (1988)) and those chelators described in U.S. Pat. No. 4,885,363, among others.

The extracellular contrast agents of the prior art accumulate in tissue by perfusion dominated processes. As will be more fully described below, incorporation of the chelator into the delivery vehicles of the invention may involve modifying the chelator structure by appending one or more functional groups preferably to the chelator backbone. The carboxylic acid side chains of DTPA and DOTA, for example, can also be used as a site for further conjugation. However, this latter approach is not preferred because it may result in a loss in complex stability due to the replacement of one of the chelating "claws". This effect is more pronounced in DTPA, since the formation constant of the DOTA structure does not appear to decrease significantly with the loss of a single carboxylic side chain. This makes DOTA and p-aminobenzyl DOTA a preferred chelator, since, as discussed earlier, the key to exploiting the relaxation properties of an MRI contrast agent without lowering the physiological stability is to functionalize (e.g. tissue specific or metabolic probe sites) the molecule while not perturbing the binding site of the metal atom.

In addition to the MRI contrast agents described herein, the same features that make the invention advantageous for MRI are relevant to other imaging modalities. Gamma and positron emission tomography are also effective imaging technologies in clinical diagnostic use. Accordingly, contrast agents that are useful for positron emission tomography may be used in place of paramagnetic chelates to enhance images and include [19]fluorine and [11]carbon or chelates emitting gamma particles such as [51]chromium, [68]gallium, [99]technetium and [111]indium. In addition, contrast agents for optical and fluorescence microscopy can also be used. Especially useful agents for such applications include fluorescein and rhodamine and their derivatives. See for example the list of modified dextrans and polylysines on pages 116–118 of Molecular Probes Inc., Handbook of Fluoroscent Probes and Research Chemicals, Haugland, 1989 Catalog. These polymers are modified with common dyes such as aminocoumarin, Cascade Blue, coumarinamino, dansyl, dichlorofluorescein, dimethylfluorescein, fluorescein, bodipy, phycobiliproteins such as allophycocyanin and phycoerythrin, Texas Red, and Lucifer Yellow.

In addition, several optical contrast agents may also be used. These optical contrast agents may also serve as therapeutic agents, as is described below. These agents, include, but are not limited to, derivatives of the porphyrins, anthraquinones, anthrapyrazoles, perylenequinones, xanthenes, cyanines, acridines, phenoxazines and phenothiazines [Diwu, Z. J. and Lown, J. W., *Pharmacology and Therapeutics* 36: 1–35 (1994); Grossweiner, L. I., *American Chemical Society Symposium Series* 559: 255–265 (1994)].

In addition to the contrast agents outlined above, the physiological agents of the invention may include therapeutic agents. By "therapeutic agents" herein is meant agents that have a physiological effect on the cells to which they are delivered.

In a preferred embodiment, the therapeutic agents are harmful or toxic to cells, thus allowing the selective inhibition, destruction or death of particular cells. This is particularly useful when the targeting moiety, described below, is specific for tumor cells. In this manner, the delivery vehicles are targeted for tumor cells, and the attached therapeutic agents selectively kill the tumor cells upon contact with or entry into the cell. In this way, the delivery vehicles of the present invention allow a reduction in systemic toxicity of certain therapeutic agents, particularly anti-cancer agents.

Preferred therapeutic agents of this embodiment include, but are not limited to, anti-cancer agents, enzyme inhibitors, phototherapeutic agents, radiopharmaceuticals, transcription factors, ligands, peptides, and proteins including viral proteins and so-called "tumor suppressor" proteins.

In a preferred embodiment, the therapeutic agent is an anti-cancer agent. In this manner, the systemic toxicity of the anti-cancer agent is decreased, since the targeting of the vehicle for tumor cells minimizes any systemic delivery. Preferred anti-cancer or anti-tumor agents include, but are not limited to, cisplatin, carboplatin, tetraplatin, taxol, melphalan, 5-fluorouracil, azacytadine, cytarabine, meraptopurine, methotrexate, thioguanine, podophyllin, vincristine, vinblastine, bleomycin, busulfan, cyclophosphamide, mechlorethamine, thiotepa, azathioprine, carmustine, chlorambucil, iomustine, cyclophosphamide, procarbazine, doxorubicin, daunorubicin, dactinomycin, plicamycin, mitomycin, idarubicin, diethylstilbestrol, taxoxifen, megestrol, leuprolide, bromocriptine, aminogluthethimine, and mitotane.

In a preferred embodiment, the therapeutic agent is a tumor suppressor protein or "growth regulator" protein. Suitable proteins include, but are not limited to, adenovirus E1A oncoprotein, the product of the retinoblastoma susceptibility gene pRB, the SV40 T-antigen, the human papillomavirus E7 protein, p53, and the viral oncoproteins p107, p130 and p300 (see Hung et al., *Gene* 159:65–71 (1995); Ludlow et al., *Virus Res.* 35:113–121 (1995)).

In a preferred embodiment, the therapeutic agent may be an enzyme inhibitor. As is appreciated in the art, some enzyme inhibitors are also anti-cancer agents. Particularly preferred enzyme inhibitors include inhibitors of enzymes of the DNA and RNA replication pathway, such as ricin (ricin III or ricin IV), and α-amanitin; the protein synthetic pathway, such as cycloheximide; and in particular, anti-viral or anti-bacterial enzymes such as rifampicin. Also included are inhibitors of cellular and viral proteases such as HIV protease and inhibitors of cellular and viral kinases inlcuding tyrosine kinases. Specifically included are the "suicide peptides" that competively inhibit tyrosine kinases (see Thomas et al., *Rev. Oncology* 4(1)107 (1991)).

In one embodiment, the therapeutic agent is a phototherapeutic compound such as is generally described in Grossweiner, supra, and Diwu, supra, both of which are expressly incorporated by reference herein. As noted above, some optical contrast agents may be considered therapeutic agents, due to their photosensitivity characteristics. Thus, photodynamic therapeutic agents generally act by generating singlet oxygen, peroxides, hydroxy radical, superoxide anion radicals or other oxygenated products upon exposure to light in the "photodynamic window" (approximately 550 to 800 nm). These products are extremely detrimental to living cells. There are a large number of suitable phototherapeutic agents, including, but not limited to, anthraquinones, including anthracyclines, anthracenediones, and anthrapyrazoles; perylenequinones, porphyrins, including hematoporphyrins and hematoporphyrin derivatives; anthrayrazoles, xanthenes, cyanines, acridines, phenoxazines, and phenothiazines. In a preferred embodiment, the phototherapy agent is hematoporphyrin, which has been approved in Canada as a photodynamic therapy (PDT) agent.

In a preferred embodiment, the therapeutic agent is a radiopharmaceutical compound. Radiopharmaceutical agents such as $^{125}I$, $^{131}I$, $^{123}I$, $^{111}I$, $^{90}Y$, $^{212}Bi$, $^{213}Bi$, $^{99m}Tc$, $^{186}Re$, $^{188}Re$, $^{177}Lu$ and $^{153}Sm$.may be attached using well known techniques. See for example Wu et al., *Bioorganic Med. Chem. Letts.* 4(3):449–454 (1994); Larson, *Cancer Suppl* 1991 67:1253–1260; Schott et al., *Cancer Supp.* 73:993–998 (1994); Jurcic et al., *Curr. Op. Immunol.* 6:715–721 (1994)). The radioisotopes may be chelated if necessary, for example using DOTA and DTPA; see Schott et al., supra.

In an additional embodiment, the therapeutic agents are used to increase cell viability. For example, interferons and other cytokines such as the interleukins, growth factors and colony stimulating factors and their agonists and antagonists. See Thomas et al., supra.

In another embodiment, a single species of physiological agent is attached to the delivery vehicles of the invention. That is, a single type of contrast agent or therapeutic agent is attached, although, as outlined below, each vehicle will have a large number of agents attached. In an alternate embodiment, more than one species of physiological agent is attached to each delivery vehicle. For example, both contrast agents and therapeutic agents may be attached to a single vehicle. Alternatively, several different types of therapeutic agents or contrast agents may be attached.

In addition to the polymeric molecules and physiological agents, the delivery vehicles comprise a cell targeting moiety. One of the first or second polymeric molecule has attached to it at least one cell targeting moiety (4) that renders the delivery vehicles of the invention cell or tissue specific. The selection of cell targeting moiety will depend upon the particular cell or tissue to be targeted. The invention is exemplified below using transferrin as the targeting moiety, to which growing cells have surface receptors. However, any targeting moiety can be utilized in the invention as long as it is capable of being either directly or indirectly attached to the second polymeric molecule and of being specifically bound to and in some cases taken into a targeted cell. For example, suitable targeting moieties include, but are not limited to, antibodies, protein and glycoprotein ligands, viral receptors and targets, hormones, peptides, carbohydrates, glycolipids as well as ligand analogs, and drugs and toxins with cell and tissue specific distributions.

In a preferred embodiment, the targeting moiety is a ligand for a cell surface receptor. Preferably, the cell surface receptor is displayed in large numbers (for example, at least about $10^5$ per cell. Preferred cell surface receptors and/or cell surfact receptor ligands include, but are not limited to, transferrin, asialoglycoprotein, acetylcholine, enkephalins, endorphins, the protein responsible for low-density lipoprotein (LDL) receptor binding, hormones such as insulin, thyroid-stimulating hormone, adreocoticotropic hormone, luteinizing hormone, epinephrine, vasopressin, immune system markers such as those associated with autoimmune disorders including rheumatoid arthritis CD4, CD5, CD7, CD25, CD33, and CD54, and those associated with leukemia such as CD5, CD19 and CD22 (see Uckun, *British J. of Haematology* 85:435–438 (1993); Uckun et al., *Science* 267: 886–891 (1995)). Known tumor antigens also include ERB B2, FMS, H4-RET, TPR-MET, RET, TRK-TM, IGH-IGK, TCRαIGH (see Urban et al., supra).

In a preferred embodiment, the cell targeting moiety is an antibody, preferably a monoclonal antibody. In one embodiment, the monoclonal antibody is directed against a tumor-associated antigen, as above. As is known in the art, a large number of such antibodies exist, and are currently in use to screen biopsy tissue as well as in cancer immunotherapy (see Urban et al., *Ann. Rev. Immunol.* 10:617–644 (1992); Kemshead et al., *J. Royal Soc. Med.* 86:219–224 (1993), and Jurcic et al., supra, among others). For example, anti-TAG72 antibody B72.3 (see King et al., supra) or CC49 (Schott et al., supra), 3F8, T101 and anti-CEA (Larson et al., supra), antirenal cell carcinoma antibody A6H (see Wilbur et al., supra), 2E4 (Wu et al, *Bioorganic & Medicinal Chemistry Letters* 4(3):449454 (1994)) and antibodies disclosed in Jurcic et al., supra, expressly incorporated by reference, are useful. Preferably, the monoclonal antibodies are IgG class antibodies with high specificity towards a cell surface exposed epitope such as a cell surface receptor. As above, the exposed epitope preferably is displayed in large numbers (at least about $10^5$ per cell). As will also be appreciated in the art, active fragments of antibodies are also useful in practicing the invention.

In a preferred embodiment, the antibodies or active fragments thereof are directed against $CD_{19}$, a B lymphocyte marker not found on hematopoietic stem cells. As is known in the art, immunotherapeutic agents targeted against $CD_{19}$ have been successfully used to destroy B-cell lymphomas without causing long-term immunosuppression; see Uckun et al., *Science*, supra. In this embodiment, the $CD_{19}$ antibodies or active fragments are used as the cell targeting moiety. In a preferred embodiment, the delivery vehicles which utilize $CD_{19}$ antibodies are toxic to the targeted cells; for example, they may include nucleic acid encoding the tk gene, or may utilize a cell toxin as a therapeutic agent.

In one embodiment of the invention, the contrast agent delivery vehicle does not have a cell-targeting moiety and in general is not cell or tissue specific. In this embodiment, the polymeric molecule having a net positive charge is preferably modified to incorporate hydrophobic residues which facilitate cellular uptake. Cellular uptake of complexes of nucleic acids and polycations having hydrophobic backbones are known in the art [Jean-Paul Behr, *Bioconjugate Chemistry* 5: 382–389 (1994)]. In another embodiment of the invention, the contrast agent delivery vehicle has both a cell-targeting moiety (to generate cell and tissue-specificity) and hydrophobic residues to enhance transfection efficiency.

Once the cell targeting moiety and physiological agents are chosen, the preparation of the delivery vehicles of the invention proceeds as outlined below. In a preferred embodiment, the delivery vehicles are constructed as follows. The cell targeting moieties are added to the polymeric molecule, using the techniques below. This attachment is preferably covalent, such that the targeting moiety is permanently attached without a significant loss in its targeting ability. The polymer with the cell-targeting moieties attached is then used in the reaction adding the physiological agent. As will be appreciated by those in the art, the delivery vehicles of the invention may be made in a variety of ways using a variety of methods; the methods disclosed below are not exclusive.

The number of cell-targeting moieties per complex can vary from 0 (such as when hydrophobic polycations are used for nonspecific DNA transformation) to more than 1,000 cell-targeting moieties per delivery vehicle. A preferred number of cell-targeting moieties per complex is generally from about 10 to about 50 depending on the size of the complex. In a preferred embodiment, the ratio of targeting moiety to monomer unit of the polymer is generally about 1 to 100; for example, where transferrin is used as the cell-targeting moiety and poly-L-lysine is the polycation, approximately 1 transferrin protein to about 100 lysine monomers is a preferred ratio. Polyamines such as spermine and spermidine are modified at a single nitrogen or carbon leaving a sufficient number of amines for protonation to interact with a polyanion. Histones and protamine are modified at sites not involved in ionic interactions with polyanions such as at cysteine residues in protamine.

Generally, the cell targeting moieties are attached using one of four functional groups on the targeting moiety, particularly proteinaceous targeting moieties. In a preferred embodiment, the polymer is polylysine and the cell targeting moiety is a glycosylated protein, and the carbohydrate is used for attachment. The aldehyde of the carbohydrate is made using standard techniques, and then the aldehyde is reacted with an amino group on the polymer, for example with the E-amino group of polylysine.

In an alternative embodiment, a cysteine residue of the cell targeting moiety is used for the site of attachment. There are a number of sulfhydryl reactive linkers known in the art such as SPDP, maleimides, α-haloacetyls, and pyridyl disulfides (see for example the 1994 Pierce Chemical Company catalog, technical section on cross-linkers, pages 155–200, incorporated herein by reference).

In an alternative embodiment, an amino group on the cell targeting moiety is used for attachment to an amino group of the polymer. For example, a large number of stable bifunctional groups are well known in the art, including homobifunctional and heterobifunctional linkers (see Pierce Catalog and Handbook, pages 155–200). For example, succinimidyl 3-(2-pyridyldithio)propionate (SPDP) has been added to transferrin, and then reacted with 3-mercaptopropionate-modified polylysine (see Wagner et al., *Proc. Natl. Acad. Sci. USA* 87:3410–3414 (1990), expressly incorporated herein, and the Examples).

In an additional embodiment, carboxy groups (either from the polymer or from the cell targeting moiety) may be derivatized using well known linkers (see the Pierce catalog). For example, carbodiimides activate carboxy groups for attack by good nucleophiles such as amines (see Torchilin et al., *Critical Rev. Therapeutic Drug Carrier Systems.* 7(4):275–308 (1991), expressly incorporated herein).

Antibody cell targeting moieties may also be attached using other techniques known in the art; see Slinkin et al., *Bioconj. Chem.* 2:342–348 (1991); Torchilin et al., supra; Trubetskoy et al., *Bioconj. Chem.* 3:323–327 (1992); King et al., *Cancer Res.* 54:6176–6185 (1994); and Wilbur et al., *Bioconjugate Chem.* 5:220–235 (1994), all of which are hereby expressly incorporated by reference).

It should be understood that the cell targeting moieties may be attached in a variety of ways, including those listed above. What is important is that manner of attachment does not significantly alter the functionality of the targeting moiety; that is, the targeting moiety is still able to bind to its target cell surface receptor to cause endocytosis of the delivery vehicle. As will be appreciated by those in the art, this is easily verified.

Before or after the cell targeting moieties are attached to the polymeric molecule, the physiological agents are added. Generally it is preferred that as many physiological agents as possible be added to each delivery vehicle without adversely affecting the vehicle. Numerous physiological agents can be attached to the polyamine or to produce a polycation capable of both physiological action and of complexing to nucleic acid. Modification of up to about 20% of amino group side chains with physiological compounds and/or cell-targeting moieties leaves about 80% or more of the amino groups charged at physiologic pH for interaction with a polyanion. These ratios may be further altered if the size of the two polymeric species are different as long as significant electroneutrality is maintained. The resulting nucleic acid based physiological agent delivery vehicle contains between 1,000 and 10,000 physiological agents, orders of magnitude more than any previous strategy. In the case of contrast agents, this level of paramagnetic ions allows targeted MRI contrast enhancement at physiologically reasonable concentrations of this agent using standard MRI hardware.

Maximal numbers of physiological agents are desired without inhibition of the polycation/polyanion complex formation and without adverse toxic or osmotic effects. In general, physiological agents are attached to the polymeric molecules at a ratio of from about 1 agent per two monomers to about 1 agent per about 100 monomers, with preferred ratios ranging from about 1 agent per 4 monomers to 1 agent per 20 monomers, with from about 4 to 10 being preferred, depending on the strength of the ionic interaction of the polycation/polyanion complexes.

When the physiological agent is a contrast agent, such as an MRI contrast agent, the paramagnetic metal ion chelator, such as DTPA or DOTA is covalently attached first, and then the complex is reacted with the metal ion. The DTPA chelators are covalently attached to the polymeric molecules of the invention using well known techniques (see Hnatowich et al., *J. Immunol. Methods.* 65:147–157 (1983); Hnatowich et al., *Int. J. Appl. Radiot. Isot.* 33:327 (1982); Torchilin et al., supra; all of which are expressly incorporated by reference). In a preferred embodiment, an anhydride of the chelator is made, and is reacted with amino groups, such as those of the available lysine residues, to form an amide bond.

In addition, when DOTA is used as the chelator, it may be modified in additional ways to provide a functional group for attachment. This may be preferred in order to avoid derivatization of one of coordination atoms to avoid a loss of complex stability with resulting toxicity. For example, several literature methods have appeared for the synthetic modification of the DOTA macrocycle [Moi et al. *J. Am. Chem. Soc.* 110:6266 (1988); McMurry et al. *Bioconj. Che.* 3(2): 108 (1992); Ren et al. *Bioconj. Che.* 3(6):563 (1992); Kumar et al. *Inorg. Chem.* 32(20):4193 (1993)]. In one method, a p-aminobenzyl moiety is introduced into the DOTA ligand using a tetrapeptide starting material [Moi et al., supra]. The structure of p-aminobenzyl-DOTA is depicted in FIG. 4. The amino group of the p-aminobenzyl moiety may then be used for attachment to the polymer. The method of preparing the tetrapeptide starting material can be modified using solution methods to add a greater degree of flexibility in the synthesis of the product. The desired ligand can be prepared by variation of literature procedures. The resulting macrocyclic ligand framework fulfills the design features of a successful in vivo contrast agent. In this manner, functional groups for subsequent attachment to the polymeric molecule are added, and then the techniques outlined above for cell targeting moiety attachment can be used, such as the use of stable bifunctional linkers or carbodiimide. Other chelators may be modified to contain functional groups in a manner similar to DOTA.

When the physiological agent is a therapeutic agent, such as an anti-cancer or phototherapy agent, similar techniques are used. Proteinaceous agents or amino- or carboxy-containing agents may be attached using the techniques outlined above. For example, methotrexate, melphalan, daunorubicin, doxorubicin, cytarabine, dactinomycin, bleomycin, aminoglutethimide, mechloroehtamine, and mitomycin, among others, may be attached via an amino group. Methotrexate, melphalan, and chlorambucil may be attached via a carboxy group. Daunorubicin, doxorubicin, cytarabine, and plicamycin may be attached via the aldehyde of a carbohydrate moiety. Well known linkers may also be used. Functional groups such as amine groups may also be attached to the moiety, using well known techniques, and then appropriate linkers used. For example, phototherapeutic agents may be attached in this way.

In one embodiment, the delivery vehicles of the present invention also include other agents to increase the efficiency of gene expression. Surprisingly, when a polycomplex of DNA/poly-D-lysine/Gd-DTPA/transferrin is used to transfect cells, a higher efficiency of gene transfection is achieved than when a DNA/poly-D-lysine/transferrin complex is used that lacks an MRI contrast agent. This higher efficiency of GD-DTPA-polylysine is noticed at numerous different ratios of components (see for example FIG. 2) using both D and L isomers of the polylysine. This effect may be due to the increased uptake of Gd-DTPA containing particles or the increased efficiency of their gene expression once inside the cells.

It is known that the majority of particles are taken up via endocytosis through the receptor mediated uptake pathway, and are digested in the lysosomal compartments. Agents which promote release of particles from lysosomes are known to dramatically increase expression of delivered genes. These agents include chloroquine, viral ghosts and fusogenic peptides. In addition, proteins and peptides that translocate particles from the cytoplasm to the nucleus further enhance gene expression. Accordingly, the delivery particles of the present invention may also include agents for lysosomal release and nuclear uptake, such as an influenza virus fusogenic peptide (Wagner et al., *Proc. Natl. Acad. Sci. USA* 89:7934–7938 (1992)) and nuclear proteins such as HMG1. In addition, nuclear localization signal (NLS) peptides may be added to the vehicle for subcellular delivery to the nucleus. See for example Goldfarb et al., *Trends Cell. Biol.* 1:20–24 (1991). These additional materials are added using the techniques outlined above.

Once made, the delivery vehicles of the present invention are used in a variety of methods. In one embodiment, the delivery vehicles are used to deliver nucleic acids to a cell. The delivery vehicles comprise a nucleic acid and at least one polycationic molecule with at least one attached cell targeting moiety and an attached contrast agent. In one embodiment, a single polycationic molecule is used; in alternate embodiments, a second or multiple polycationic molecule is used, as outlined above. The delivery vehicles are contacted with a target cell, and then the presence of the nucleic acid is monitored by detecting the presence of the contrast agent. In this embodiment, the delivery vehicles comprise contrast agents, although alternatively both contrast agents and therapeutic agents can be attached.

In an additional embodiment, the delivery vehicles are used to deliver physiological agents. In one embodiment, contrast agents are delivered. In an alternate embodiment, therapeutic agents are delivered, or both contrast and therapeutic agents are delivered. In this embodiment, the delivery vehicle comprises a first polymeric molecule and a second oppositely-charged polymeric molecule. Either or both of the polymers have attached cell targeting moieties and physiological agents. The delivery of the physiological agent is detected using the presence of the physiological agent. It is preferred that MRI contrast agents are used, and monitored or detected using standard MRI techniques. In this embodiment, a nucleic acid encoding a reporter gene may also be used, and delivery detection may be done using the presence or absence of the reporter gene or protein.

In a preferred embodiment, the delivery vehicles are used to detect and/or treat tumors. In this embodiment, the delivery vehicles comprise polymeric molecules with cell targeting moieties and physiological agents attached. The cell targeting moieties are preferably specific to tumor cell receptors, or alternatively are targeted to receptors preferentially found in tumors or fast growing cells. When the delivery vehicles are used to detect or image tumors, the physiological agents are preferably contrast agents, and preferably MRI contrast agents. When the delivery vehicles are used to treat tumors, the physiological agents are anti-cancer or phototherapy agents. In a preferred embodiment, the delivery vehicles used to treat tumors also incorporate contrast agents for the real time monitoring of the therapy.

The delivery vehicles of the invention are administered to a patient or subject as is known in the art. Generally, the delivery vehicles are supplied to a patient as known contrast agents are provided, including intraveneously and subcutaneously. In some cases, for example, for lung epithelial delivery, the particles may be aerosolized and inhaled. Delivery of the vehicles may be monitored in several ways. Attached contrast agents may be observed using well known imaging techniques. Gene delivery of therapeutics or reporter genes may be monitored using standard molecular biology and protein techniques, or, in the case of therapeutics, by the effect on the targeted cells.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

Preparation of Transferrin-Poly-L-Lysine

Human apo-transferrin was purified by size exclusion chromatography and dissolved in 30 mM sodium acetate buffer (pH 5.0). At 4° C., 20 molar equivalents of sodium periodate were added. The reaction to oxidize the transferrin carbohydrate (N-acetylneuraminic acid) to its aldehyde form, was allowed to proceed at 4° C. for 120 minutes. The modified transferrin was purified by size-exclusion chromatography and added immediately to a solution containing 0.5 equivalents poly-L-lysine (average chain length=180 subunits) in 100 mM sodium acetate buffer (pH 5.0). The reaction product was reduced to the secondary amine with the addition 800 equivalents of sodium cyanoborohydride in four aliquots at 1 hour intervals [Wagner et al., *Proc. Natl. Acad. Sci. USA* 89:7934–7938 (1992)].

The transferrin modified poly-L-lysine was fractionated by size-exclusion chromatography. The fraction determined to contain polylysine modified with on average 2 transferrin molecules per polycation chain was used in subsequent experiments.

Example 2

Preparation of DTPA-Poly-D-Lysine

The conjugation of polylysine with DTPA dianhydride was accomplished using modifications of standard literature procedures [Hnatowich et al., *J. Immunol. Methods* 65:147–157 (1983)]. Polylysine modified at 5 to 20% of the monomer sidechains was prepared in order to balance the desire for high signal strength of the Gd-containing particles against the need to maintain the DNA binding capacity of the polycationic chain.

Fifty milligrams of poly-D-lysine (average chain length=180 subunits) was dissolved in 20 ml of 0.5M sodium carbonate buffer (pH 9.8), and placed in a 50 ml round bottom flask equipped with a stirring bar. Freshly prepared DTPA anhydride was added (100, 200 and 400 fold equivalent excess in separate reactions) in 10 equal portions over a period of 1 hour. The pH of the reaction was maintained at 9.8 by the addition of 3% sodium hydroxide solution. The DTPA modified poly-D-lysine was purified by size exclusion chromatography employing a Pharmacia FPLC system.

In order to evaluate the number of DTPA molecules per lysine chain, aliquots of the purified product were allowed to react with $EuCl_3$ in water. Fluorescence emission measurements of the products (612 nm) were performed on a SLM 8000C spectrofluorimeter versus a series of standards. The total amount of substituted derivatives ranged from 9–11 DTPA/polylysine for the 100 fold excess reaction product to 35 DTPA/polylysine for the 400 fold reaction. The Eu-DTPA-polylysine from each reaction were tested for their ability to bind DNA using a UV hyperchromicity assay in which DNA complexed with polycations shows higher absorbance of UV light than uncomplexed DNA. Using this assay, it was found that the least heavily modified polylysine (10 $Eu^{3+}$'s per polylysine) bound DNA as well as unmodified polylysine; the most heavily modified polylysine did not bind DNA at all; and the moderately labeled polylysine showed reduced DNA binding affinity.

The compound with an average 10 DTPA sites per polylysine was allowed to chelate with a 1.1 molar excess of Gd(CI)$_3$ in distilled water at pH 7.0 for 3 hours at 70° C. The Gd-DTPA-poly-D-lysine was purified by gel filtration and used in subsequent experiments.

Example 3

Formation of Tissue-Specific/MRI Contrast Agent Complex

The "GeneLight" plasmid was purchased from Promega Corp. (Madison, Wis.) and prepared in large quantities using standard procedures. This plasmid contains the luciferase gene (*P. pyralis*) under the control of the SV40 enhancer/promoter resulting in strong luciferase expression in mammalian cells, such as the K562 human line used in this study. The expression of this gene is easily monitored by measuring light production in extracts of transfected cells.

Typically, 6 µg of plasmid was added to suboptimal quantities of transferrin-polylysine in 0.5 ml HEPES buffered saline (150 mM sodium chloride, 20 mM HEPES, pH 7.3) and allowed to form complexes for 10 minutes at room temperature [Wagner et al., *Proc. Natl. Acad. Sci. USA* 88:4255–4259 (1991)]. Varying amounts of poly-D-lysine or Gd-DTPA-poly-D-lysine were added to the solution to completely neutralize the negative charge by forming ternary complexes with the DNA.

Example 4

DNA Expression in Targeted Cells

K562 cells were grown in suspension in RPMI medium plus 10% fetal calf serum, 100 units/ml penicillin, 100 µg/ml streptomycin and 2 mM glutamine. The Gd-DTPA-polylysine/DNA/transferrin-polylysine complexes formed were added to 2 ml of a cell suspension containing 500,000 cells and 100 µM chloroquine, and allowed to incubate at 37° C. for 10 hours. As a control, some cells were simultaneously treated with free transferrin to competitively inhibit the receptor mediated uptake of the MRI contrast agent delivery vehicle. Subsequently the cells were washed into fresh medium and harvested after 18 hours. Cells were washed three times with HEPES buffered saline and lysed in 30 µl of extract buffer.

Immediately after addition of the luciferase substrate and adenosine triphosphate, light emission was assayed with a Beckman scintillation counter. FIG. 2 compares graphically the levels of gene expression observed using gene delivery vehicles which contain Gd-DTPA poly-D-lysine (column 1) with gene delivery vehicles that contain unmodified poly-L-lysine instead of the contrast agent. The addition of the Gd chelate to the polylysine actually enhances the efficiency of gene transfection, an observation noted at other particle compositions as well. With the addition of 20 µg of free transferrin to these experiments, light production indicating efficiency of gene transfection is dramatically reduced (column 3). This effect indicates that the mechanism of gene transfection is indeed transferrin mediated uptake.

Example 5

MRI Image Acquisition

MRI images were acquired using a 11.7 Tesla Bruker AMX 500 MHz MRI spectrometer with microimaging accessory. Suspensions of cells identical to those used to assay transfection efficiency were used to obtain the images shown in FIG. 3. Approximately 500,000 cells were transferred to 2 mm glass capillary tubes and allowed to settle out of suspension. The tubes were sealed, and images were acquired using a multi-slice spin echo protocol (TR/TE=300/13 ms). These parameters result in a $T_1$ lighted image, as is appropriate for Gd based contrast agents.

In FIG. 3 the cells transfected with particles containing Gd-DTPA-poly-D-lysine are shown in 1 and 2. The addition of free transferrin in 2 competitively inhibits uptake of the particles and reduces the MRI contrast. This further confirms that MRI contrast enhancement of these particles is specific and via the transferrin uptake pathway. Thus, the cells treated with particles composed of DNA, transferrin, Gd-DTPA and polylysine show simultaneously efficient gene transfection as well as dramatic MRI contrast enhancement.

All documents referred to herein are hereby expressly incorporated by reference.

What is claimed is:

1. A delivery vehicle comprising:
    a. a deoxyribonucleic acid (DNA) polymer;
    b. a poly-L-lysine polymer conjugated to transferrin;
    c. a poly-D-lysine polymer conjugated to diethylenetriaminepentaacetic acid (DTPA); and
    d. said DTPA chelates a gadolinium ion.
2. A delivery vehicle comprising:
    a. a DNA polymer;
    b. transferrin;
    c. DTPA, wherein said DTPA chelates a gadolinium ion; and
    d. a polylysine polymer.
3. A delivery vehicle comprising:
    a. a first poly-L-lysine polymer;
    b. a second poly-L-lysine polymer conjugated to transferrin; and
    c. a DNA polymer.

* * * * *